US00PP19364P2

(12) United States Plant Patent
Probst

(10) Patent No.: US PP19,364 P2
(45) Date of Patent: Oct. 21, 2008

(54) ***COREOPSIS* PLANT NAMED 'FULL MOON'**

(50) Latin Name: *Coreopsis*
Varietal Denomination: Full Moon

(76) Inventor: Darrell R. Probst, 63 Williamsville Rd., Hubbardston, MA (US) 01452-1315

( * ) Notice: Subject to any disclaimer, the term of this patent is extended or adjusted under 35 U.S.C. 154(b) by 0 days.

(21) Appl. No.: 11/982,547

(22) Filed: Nov. 2, 2007

(51) Int. Cl.
*A01H 5/00* (2006.01)

(52) U.S. Cl. ..... Plt./417

(58) Field of Classification Search ..... Plt./417
See application file for complete search history.

(56) References Cited

U.S. PATENT DOCUMENTS

PP16,906 P3 * 8/2006 Delbard ..... Plt./132

* cited by examiner

*Primary Examiner*—Wendy C. Haas
(74) *Attorney, Agent, or Firm*—Penny J. Aguirre

(57) ABSTRACT

A new cultivar of hybrid *Coreopsis* named 'Full Moon' characterized it's large, bright yellow flowers with overlapping ray florets, its sturdy stems, its clumping plant habit, its vigorous growth habit, and its perennial habit and cold hardiness to at least to U.S.D.A. 5.

2 Drawing Sheets

Botanical classification: *Coreopsis* hybrid.
Variety denomination: 'Full Moon'.

BACKGROUND OF THE INVENTION

The present invention relates to a new and distinct cultivar of *Coreopsis* plant, botanically of hybrid origin and known as *Coreopsis* 'Full Moon' and will be referred to hereinafter by its cultivar name, 'Full Moon'. The new cultivar of *Coreopsis* is an herbaceous perennial growth for landscape and container use.

The new invention arose from an ongoing controlled breeding program in Hubbardston, Mass. the objective of the breeding program is to develop hybrid cultivars of *Coreopsis* with unique and superior garden attributes. In particular, to develop cultivars that are long-lived, sturdy, exhibit a true perennial habit and cold hardy to at least U.S.D.A. Zone 5 in a wide range of flower colors and plant forms. The inventor collected seed in the wild from five different species that are not commercialized and made six generations of crosses to produced interspecific hybrids to utilize in his breeding work.

The inventor made a cross in 2005 in Hubbardston, Mass. under controlled conditions between an unnamed F1 hybrid between *Coreopsis rosea* and an interspecific hybrid from his breeding program as the female parent and an unnamed plant of hybrid *Coresopsis* from his breeding program as the male parent. Neither parent is patented. 'Full Moon' was selected in 2006 as a single unique plant amongst the resulting seedlings.

Asexual reproduction of the new cultivar was first accomplished by stem cuttings in a controlled environment in Hubbardston, Mass. in July of 2006 by the inventor. The characteristics of this cultivar have been determined to be stable and are reproduced true to type in successive generations.

SUMMARY OF THE INVENTION

The following traits have been repeatedly observed and are determined to be the characteristics of the new cultivar.

These attributes in combination distinguish 'Full Moon' as unique from all *Coreopsis* cultivars and species known to the inventor.

1. 'Full Moon' exhibits large composite flowers up to 7.6 cm (3 inches) in diameter.
2. 'Full Moon' exhibits composite flowers with overlapping ray florets that are bright canary yellow in color.
3. 'Full Moon' exhibits sturdy stems.
4. 'Full Moon' has a clumping plant habit.
5. 'Full Moon' exhibits a vigorous growth habit.
6. 'Full Moon' is cold hardy at least to U.S.D.A. Zone 5.

'Full Moon' differs from its female parent in that the female parent has weaker stems, a more lax plant habit and flowers that are smaller and paler yellow in color. The male parent differs from 'Full Moon' in having dark yellow flowers with a much shorter blooms period. 'Full Moon' can be compared to *Coreopsis* 'Moonbeam' (not patented) and *Coreopsis 'Créme Brulee' (U.S. Plant Pat. No.* 16,096). Both exhibits flowers that are similar in color to 'Full Moon'. 'Full Moon' differs from 'Moonbeam' in having larger brighter colored flowers, overlapping ray florets, and a clump forming plant habit. 'Full Moon' differs from 'Créme Brulee' in having larger flowers, much sturdier plant habit, and in having a true perennial growth habit in U.S.D.A. Zone 5.

BRIEF DESCRIPTION OF THE DRAWING

The accompanying colored photographs illustrate the overall appearance and distinct characteristics of the new *Coreopsis.*

The photograph in FIG. 1 was taken on a six month old plant of 'Full Moon' as grown in a one gallon.

Figure 1:
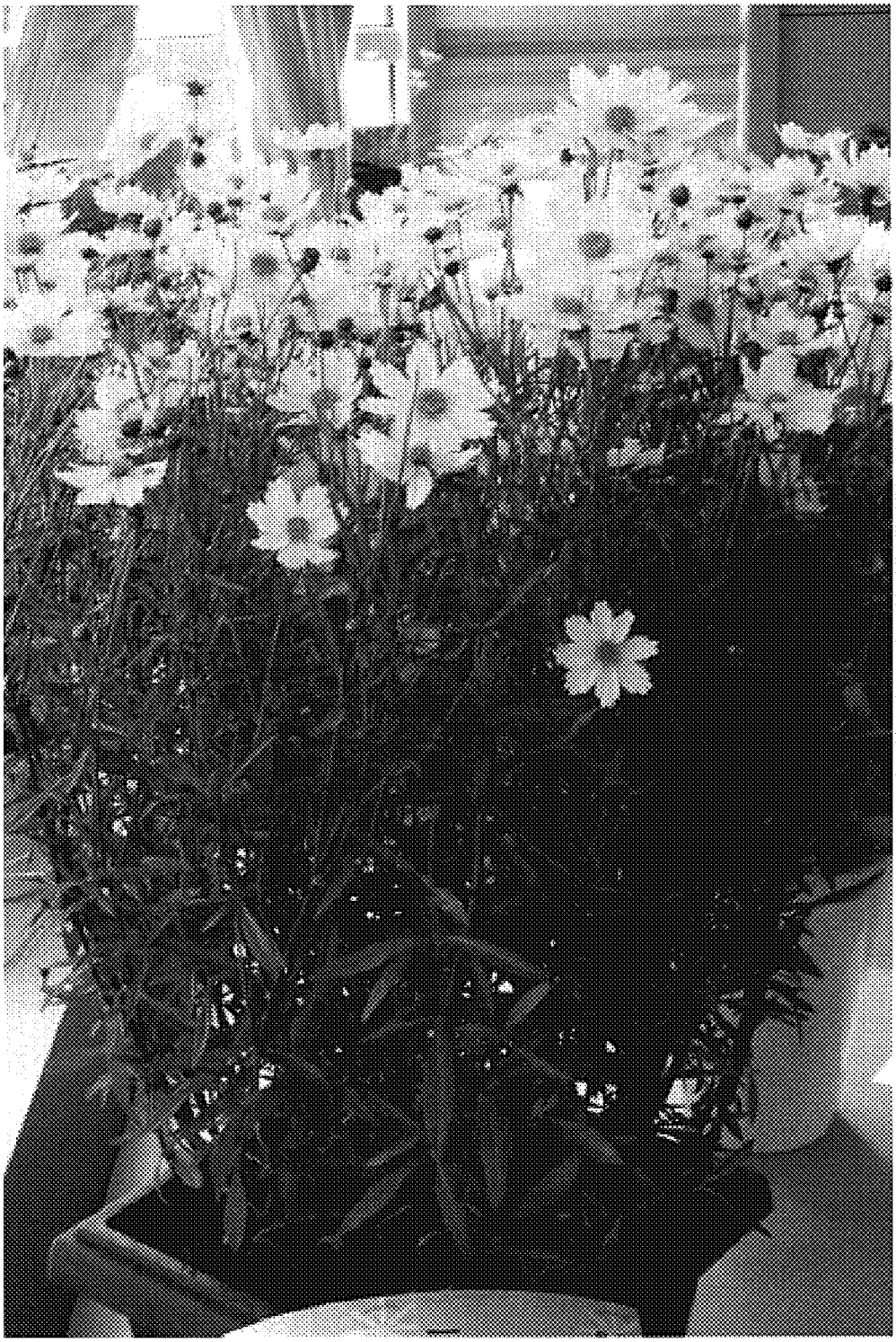
Figure 2:
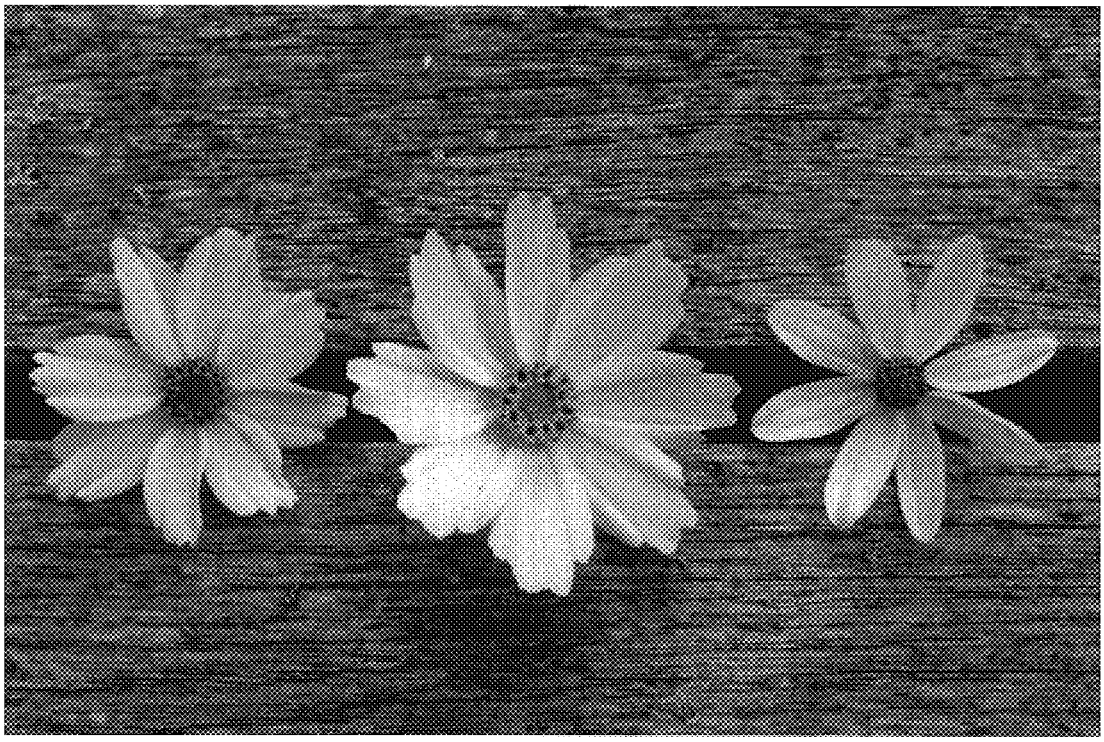

The photograph in FIG. 2 was taken of flowers from 4 month-old plants as grown in one gallon containers in Hubbardston, Mass. and provides a close-up view of a flower of 'Full Moon' (center) in comparison to a flower of 'Créme Brulee' (left) and 'Coreopsis Moonbean' (right).

Figure 3:
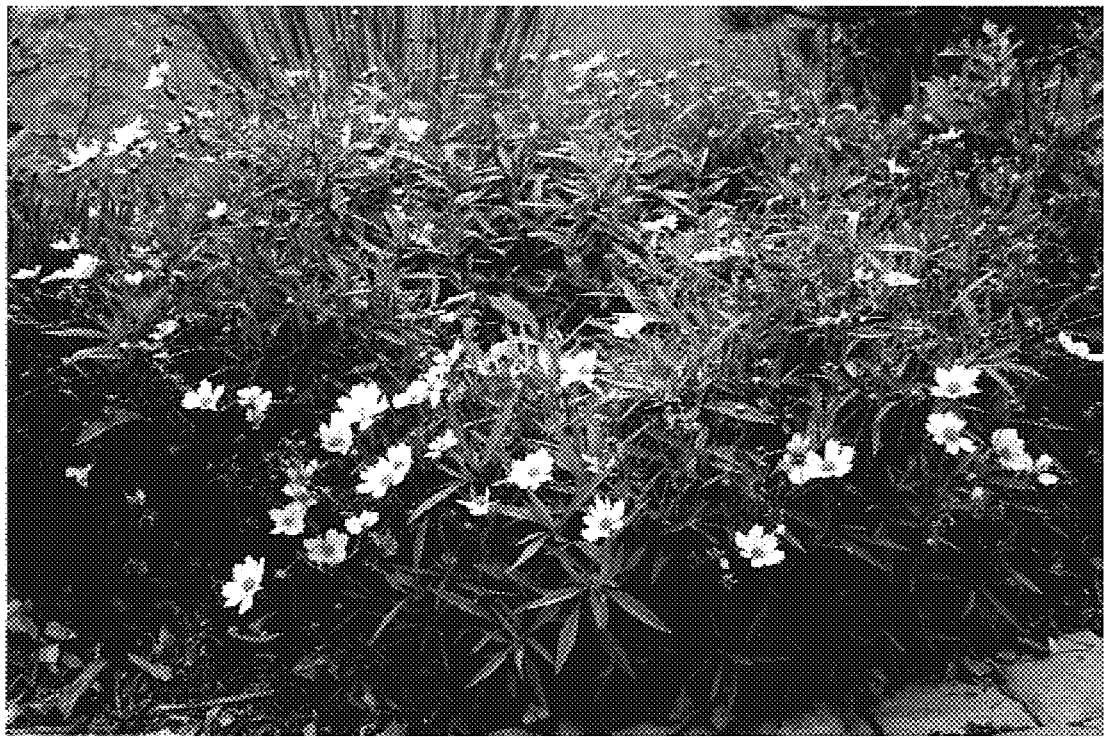

The photograph in FIG. 3 was taken in September of a plant grown in a trial bed in Minnesota for 3 months from a one-gallon container.

The colors in the photographs are as close as possible with the photographic and printing technology utilized. The color values cited in the detailed botanical description accurately described the colors of the new *Coreopsis*.

DETAILED BOTANICAL DESCRIPTION

The following is a detailed description of the new cultivar as observed for one year in a trail beds in Hubbardston, Mass. and New Hope, Minn. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General Description:

*Blooming period.*—Blooms from late July until frost in central Massachusetts.

*Plant habit.*—Herbaceous perennial, clump forming, mounded.

*Height and spread.*—Reaches 60 to 75 cm (24 to 36 inches) in height and 76 to 91 cm (30 to 36 inches) in width.

*Cold hardiness.*—At least to U.S.D.A. Zone 5, has not been tested in colder regions.

*Culture.*—Tolerant to a wide range of growing conditions, growing well in full sun to light shade, in dry to moist soils if well-drained, performs well in containers.

*Diseases resistance.*—More resistance to powdery mildew has been observed in comparison to *Coreopsis grandiflora* cultivars grown under the same conditions.

*Root description.*—Fibrous, fine and well-branched.

Growth and Propagation:

*Propagation.*—Terminal stem cuttings and division.

*Growth rate.*—Vigorous.

Stem description:

*Shape.*—Tetragonal, solid.

*Stem color.*—144A with mature stems flecked with 165A.

*Stem size.*—Main stem averages 24 cm in length with laterals an average of 15 cm in length (excluding peduncles), average of 3.5 mm in width.

*Stem surface.*—Glabrous when young, ridged and sparsely covered with translucent hairs when mature.

*Branching habit.*—Freely branched, typically branched as opposite laterals at each node, average of 7 branches per main stem, pinching is not required for branching, branch internode about 5 cm in length.

Foliage description:

*Leaf division.*—Simple.

*Leaf margins.*—Palmately dissected into three lobes or entire, lobes are entire.

*Leaf size.*—Average of 4.5 cm in length and 3 cm in width when trifid and an average of 4 cm in length and 4 mm in width when entire, or trifid leaves; center lobes average 3.5 cm in length and 5 mm in width, lateral lobes average 2 cm in length and 3 mm in width.

*Leaf shape.*—Lanceolate when entire and trifid lobes are lanceolate to ligulate.

*Leaf base.*—Cuneate.

*Leaf apex.*—Acute.

*Leaf venation.*—Only midrib is visible, not conspicuous, coloration same as leaf.

*Leaf attachment.*—Sessile.

*Leaf arrangement.*—Opposite.

*Leaf surface.*—Dull and puberulent on upper surface and satiny and puberulent on lower surface.

*Leaf color.*—Young and mature; upper 137A, lower 137B.

Flower description:

*Inflorescence type.*—Campitulum with ray florets surrounding disk florets in the center, forming a radiant head, inflorescences are borne on terminals arising from leaf axils, in loose open clusters of 2 to 5 capitulums per lateral branch.

*Lastingness of inflorescence.*—About one week until senescence of ray flowers, bracts and disk flowers are persistent.

*Fragrance.*—None detected.

*Quantity of inflorescences.*—Very free flowering, over 200 per one year-old plant.

*Inflorescence size.*—Average 1.5 cm in depth and up to 7.6 cm in diameter with disk portion up to 2 cm in diameter.

*Inflorescence buds.*—Average of 1 cm in depth and diameter, shape is spherical, color is a color between 12A and 14A suffused with 144A towards base.

*Peduncle.*—Strong, average of 16 cm in length and 1.2 mm in diameter, 144A in color, glabrous surface.

Involucral bracts:

*Bract number.*—Two rows of 8.

*Bract arrangement.*—Outer bracts are unfused and held at about a 45° angle when flower is fully opened becoming horizontal after ray florets drop, inner bracts overlap and surround receptacle with apical portion spreading (campanulate-like).

*Bract size.*—Outer bracts about 6.5 mm in length and 2 mm in width, inner bracts about 1 cm in length and 3.5 mm in width.

*Bract color.*—Outer bracts 137C in both surfaces, inner bracts; base 144A with apical region 7A.

*Bract texture.*—Glabrous, inner bracts waxy.

*Bract apex.*—Acute.

*Bract base.*—Truncate.

*Bract shape.*—Outer bracts lanceolate, inner bracts broadly lanceolate.

Ray florets (sterile):

*Number.*—8.

*Shape.*—Obovate, appearance of three longitudinal sections.

*Size.*—Up to 3 cm in length and 2 cm in width.

*Apex.*—Emarginate with 3 notches.

*Base.*—Broadly cuneate.

*Margins.*—Entire on sides, notched on apex.

*Aspect.*—Held flat, perpendicular to peduncle.

*Texture.*—Glabrous on both surfaces.

*Color.*—Upper and lower surfaces when fully open; closest to 14A to 15A, upper and lower surface at petal drop; 21A.

Disk flowers (male and female):

*Shape.*—Tubular, corolla is fused, flared at apex.

*Size.*—About 6 mm in length and 2 mm in width.

*Color.*—In masse; 17A when fully open and maturing to 165A when ray florets drop, corolla; base (tube) is 150C in color, flared portions is 11A and translucent.

*Recepticle.*—About 5 mm in diameter and 1.5 mm in depth, 144C to 144D in color.

Reproductive organs:

*Presence.*—Disk flowers are perfect, ray flowers sterile.

*Gynoecium.*—1 Pistil, 5 mm in length, style is very fine and 150C in color, bifid pillose stigma is 163A in color with branches about 1.5 mm in length and recurved, ovary is 2 mm in length, 1 mm in width, placement is inferior, translucent and 144D in color.

*Androcoecium.*—5 stamens, fused into tube surrounding style, 3 mm in length and 0.7 mm in width, about 202A in color, no pollen was observed.

*Fruit.*—No fruit development was observed.

It is claimed:

1. A new and distinct cultivar of *Coreopsis* plant named 'Full Moon' as herein illustrated and described.

* * * * *